US005614596A

United States Patent [19]
Laine et al.

[11] Patent Number: 5,614,596
[45] Date of Patent: *Mar. 25, 1997

[54] DOUBLE ALKOXIDE MONOMERS OLIGOMERS AND POLYMERS

[75] Inventors: Richard M. Laine; Clint R. Bickmore, both of Ann Arbor; Kurt F. Waldner, Belleville, all of Mich.

[73] Assignee: Regents of University of Michigan, Ann Arbor, Mich.

[*] Notice: The term of this patent shall not extend beyond the expiration date of Pat. No. 5,418,298.

[21] Appl. No.: 371,911

[22] Filed: Jan. 12, 1995

Related U.S. Application Data

[63] Continuation-in-part of Ser. No. 34,531, Mar. 19, 1993, Pat. No. 5,418,298.

[51] Int. Cl.$^6$ .......................... C08G 79/10; C08G 77/02
[52] U.S. Cl. .................. 525/389; 528/395; 556/443; 556/173; 556/179; 556/9; 556/28; 556/81; 556/27; 556/1; 549/4; 549/3
[58] Field of Search ......................... 528/395; 525/389; 556/443, 173, 179, 9, 28, 81, 27; 549/4, 3

[56] References Cited

U.S. PATENT DOCUMENTS

| | | | |
|---|---|---|---|
| 3,455,980 | 7/1969 | Frye | 260/448.8 |
| 5,099,052 | 3/1992 | Laine et al. | 556/443 |
| 5,418,298 | 5/1995 | Laine et al. | 525/389 |

OTHER PUBLICATIONS

"Synthesis of Penta–alkoxy and Penta–aryloxy silicates directly from SiO$_2$", Blohosiak et al., *Inorganic and Organometallic Polymers with Special Properties*, pp. 99–111 (1992).

"Magnesia–Alumina–Spinel", Roger M. Evans, *American Ceramic Society Bulletin*, pp. 59–63.

"X–Ray Photodetection Spectroscopy Investigation of MgAl$_2$O$_4$ Thin Films for Humidity Sensors", Mattogno and Righini, *J. Mater. Res.*, vol. 9, No. 6, Jun. 1994 pp. 1426–1433.

"Heterometallic Aluminum Alkoxides. The Characterization of (Mg[Al(OPr$^i$)$_4$]$_2$)$_n$ and Mg$_2$Al$_3$(OPr')$_{13}$", *Chem, Mater.* 1993, vol. 5, pp. 755–757.

"Erste Kristallstruktur Eines Gemischten Al–Mg–Alkoholates", Jörg Sabmannshausen (1993) *Z. Naturforsch*, 488, pp. 7–10 (1993).

"Alumatrane (Al(OCH$_2$CH$_2$)$^3$N: A Reinvestigation of Its Oligomeric Behavior", Jirl Pinkas and John G. Verkade, *Inorganic Chemistry* vol. 32, No. 12, 1993 pp. 2711–2716.

"Pentacoordinate Silicon Compounds V.$^{1a}$ Novel Silatrane Chemistry", Frye, et al *Journal of the American Chemical Society*, 93:25, Dec. 15, 1971, pp. 6805–6811.

"Pentacoordinate Silicon Derivatives. IV.$^1$ Alkylammonium Siliconate Salts Derived from Aliphatic 1,2–Diols", *Journal of the American Chemical Society*, 92:5, Mar. 11, 1970, pp. 1205–1210.

"Single Molecular Precursor Metal–organic Chemical Vapor Deposition of MgAl$_2$O$_4$ Thin Films", Zhang, et al, *J. Mater. Res.*, vol. 9, No. 6, Jun., 1994, pp. 1333–1336.

"Synthesis of Pentacoordinate Silicon Complexes from SiO$_2$", Laine, et al, *Nature*, vol. 353, Oct. 17, 1991, pp. 642–644.

"Synthesis of Penta–alkoxy–and Penta–aryloxy Silicates Directly from SiO$_2$", Blohowiak, et al, *Inorganic and Organometallic Polymers with Special Properties* pp. 99–111 (1992).

"Crystal adn Molecular Structure of the Unusual Alumatrane Complex:, et al", Struckhov, et al, *Dokl Akad. Nauk SSR* (1984) 22, pp. 1185–1189.

*Primary Examiner*—Margaret W. Glass
*Attorney, Agent, or Firm*—Brooks & Kushman P.C.

[57] ABSTRACT

A process for the preparation of polymetallooxanes employing inexpensive metal sources such as sand, alumina, and rutile involves dissolving one or more group IIIa, IVa, IVb metaloxy compounds such as metal oxides, metal hydroxides, or hydrates thereof with a di- or polyhydroxyl functional compound in the presence of an amine or alkanolamine. The polymetallooxane products are anionic, neutral, or mixed neutral/anionic moieties, which, when anionic, contain a metallic counterion (cation) or an ammonium or phosphonium ion. Mixed polymetallooxanes, as well as homo polymetallooxanes which may be prepared by the subject process, are suitable for use in preparing coatings, fibers, powders, ceramics, and glasses while being easily processable and economic to manufacture.

26 Claims, 5 Drawing Sheets

DOUBLE ALKOXIDE MONOMERS OLIGOMERS AND POLYMERS

This invention was made in part with Government support under Contract Nos. DAAL-91C-0068 and DAAL01-93-M-S522 awarded by the Department of the Army. The Government has certain rights in this invention.

CROSS-REFERENCE TO RELATED APPLICATION

This application is a continuation-in-part of U.S. patent application Ser. No. 08/034,531, filed Mar. 19, 1993, which is incorporated herein by reference, and is now U.S. Pat. No. 5,418,298.

TECHNICAL FIELD

The present invention pertains to species containing M—O—R bonds and a method of making such species from compounds containing M—O—H, M—O—M, M=O and M—O—M' moieties, wherein M or M' may be B, Al, Ga, In, Si, Ge, Sn, Pb, Ti, Zr, or Hf and R is an organic moiety including alkyl, aryl, alkoxy groups, etc.. In particular, it pertains to ionic and ionic/neutral monomeric; linear, branched or cyclic oligomeric, or polymeric materials containing metal alkoxides which are suitable precursors for polymers, ceramics, and glasses. Most particularly, it pertains to materials containing tri, tetra, penta and hexacoordinate anionic, and anionic/neutral double alkoxides (polymetallooxanes), where the counterion, when present, is a group Ia or IIa metal or ammonium or phosphonium ion including $NR_4^+$ or $PR_4^+$ where R is hydrogen, or an organic moiety including alkyl, aryl, alkoxy groups, etc. The present invention further pertains to a process for the preparation of such species.

BACKGROUND ART

Metal alkoxides and aryloxides are typically produced by reaction of the metal, or its halide with the respective alcohol, aryl hydroxy compound or the corresponding salt, as illustrated in the following three reactions:

$$M + ROH \xrightarrow{catalyst} M(OR)_x + 0.5xH_2 \quad (1)$$

$$MCl_x + ROH \longrightarrow M(OR)_x + xHCl \quad (2)$$

$$MCl_x + xRONa \longrightarrow M(OR)_x + xNaCl \quad (3)$$

The pure metal, in all cases, is produced by high temperature (>900° C.) metallurgical processes or electrochemical processes as described in *The Production of Inorganic Materials,* by J. W. Evans and L. C. De Jonghe, MacMillan Pub. Co., N.Y., N.Y., 1991. The chlorides can be made via several routes as illustrated by the following three reactions:

$$M + xHCl \xrightarrow{catalyst} MCl_x + 0.5xH_2 \quad (4)$$

$$M + 0.5xCl_2 \longrightarrow MCl_x \quad (5)$$

$$FeTiO_3 + 3C + 2Cl_2 \longrightarrow TiCl_4 + 3CO + Fe \quad (6)$$

Before any metal alkoxides can be prepared, production of the starting reactants requires high temperature, energy and equipment intensive steps. The chloride routes also require toxic and polluting reactants which mandate the use of specially designed reactors. Moreover many simple alkoxides, for example $Al(OCH_3)_3$ or $Al(OCH_2CH_3)_3$, form poorly tractable polymers [see Advanced Inorganic Chem., Cotton and Wilkinson, Wiley Interescience, 5th Ed., 1988, pp. 220–1] that are difficult to handle because they are very moisture sensitive, corrosive, highly flammable and/or toxic.

Thus, typical routes to simple metal alkoxides are multistep and require excessive temperatures that waste energy and specially designed, high cost equipment. Furthermore, many of the resulting compounds are difficult to work with because of their instabilities and toxic nature.

The preparation of double alkoxides is even more complicated, as described in *Metal Alkoxides,* D. C. Bradley, R. C. Mehrotra, D. P. Gaur; Academic Press, N.Y., N.Y. (1978). Examples of double alkoxides made from metal derived alkoxides include: (1) "Erste Kristallstruktur eines gemischten Al-Mg-Alkoholates," J. Sassmannshausen, R. Riedel, K. B. Pflanz, H. Chmiel, Z. Naturforsch. (1993) 48b, 7–10, and (2) "Heterometallic Aluminum Alkoxides. The Characterization of $\{Mg[Al-(OPr^i)_4]_2\}$ and $Mg_2Al_3 (OPr^i)_{13}$," J. A. Meese-Marktscheffel, R. Fukuchi, C. M. Jensen, J. W. Gilje, Chem. Mater. (1993), 5, 755–757. The latter paper demonstrates that attempts to prepare pure Mg/Al double alkoxides via reaction (7) can lead to a mixture of products with variable stoichiometries:

$$Mg(OPr^i)_2 + Al(OPr^i)_3 \rightarrow Mg[Al(OPr^i)_4]_2 + Mg_2Al_3(OPr^i)_{13} \quad (7)$$

Mixtures of compounds and off stoichiometric compounds make processing single phase ceramics from precursors quite difficult because the processing variables can be extremely different. Furthermore, although the use of isoproxide or sec-butoxide ($OBu^i$) groups is necessary to avoid the formation of intractable polymers, these groups are much less preferable than MeO— or EtO— groups for use in preceramic polymers. This is because they contain significant quantities of carbon that must be effectively removed to form pure oxide ceramic or glass products. The potential to incorporate carbon impurities increases with increasing carbon content. Taken as a whole, monofunctional alcohol based alkoxides (e.g. $OPr^i$ ligands) are not particularly useful for preceramic polymer processing; however, the alternative, use of methoxide or ethoxide ligands is also not useful because these ligands lead to the formation of intractable polymeric precursors that cannot be further processed to useful shapes.

Cruickshank et al [a. M. C. Cruickshank, L. S. D. Glasser, "A Penta-co-ordinated Aluminate Dimer; X-ray Crystal Structure," J.C.S. Chem. Comm. (1985) 84–85. b. M. C. Cruickshank, L. S. D. Glasser, S. A. I. Barri, I. J. F. Poplett, "A Penta-co-ordinated Aluminum; a Solid-state $^{27}Al$ NMR Study," J.C.S. Chem. Comm. (1986) 23–24.] teach the synthesis of a dimeric, pentacoordinate barium aluminum alkoxides from metal derived alkoxides:

This crystalline material is not processable to any useful shape, e.g. fibers or free standing films.

An alternate approach to these materials, directly from the corresponding metal oxides or hydroxides, offers an opportunity to develop low cost, low polluting, and lower energy routes to these materials as well as novel materials without the limitations described above. For example, the reaction of silica with an alkali salt of catechol provides access to the tris(catecholato) silicate:

This reaction was first reported by Rosenheim et al [Rosenheim, A.; Raibmann, B. and Schendel, G.; Z. Anorg, Chem., 1931, 196, 160.]. Laine et al have also described the preparation of penta-and hexaalkoxysilane anions and dianions. See "Silicon and Aluminum Complexes", R. M. Laine, K. A. Youngdahl and P. Nardi, U.S. Pat. No. 5,099,052 Mar. 24, 1992; "Silicon and Aluminum Complexes", R. M. Laine, K. A. Youngdahl, U.S. Pat. No. 5,216,155, June 1993; "SiO$_2$ as a Starting Material for the Synthesis of Pentacoordinate Silicon Complexes. I.," K. Y. Blohowiak, D. R. Treadwell, B. L. Mueller, M. L. Hoppe, S. Jouppi, P. Kansal, K. W. Chew, C. L. S. Scotto, F. Babonneau, J. Kampf, R. M. Laine, *Chem. Mater.* (1994) 6, 2177–2192; R. M. Laine, K. Y. Blohowiak, T. R. Robinson, M. L. Hoppe, P. Nardi, J. Kampf, and J. Uhm, "Synthesis of Novel, Pentacoordinate Silicon Complexes from SiO$_2$," Nature (1991) 353, 642–644; "Barium Tris(glycolato)silicate, a Hexacoordinate Alkoxy Silane Synthesized from SiO$_2$." M. L. Hoppe, R. M. Laine, J. Kampf, M. S. Gordon, L. W. Burggraf, Angew. Chem. Int. (1993) 32, 287–289; and "Group II Tris(glycolato)silicate Precursors to Silicate Glasses and Ceramics," P. Kansal, R. M. Laine, J. Am. Ceram. Soc. in press. All of these compounds are also crystalline solids that are not further processable to useful shapes.

A reaction related to (8) but involving Al$_2$O$_3$ was described by Laine et al [Silicon and Aluminum Complexes, R. M. Laine, K. A. Youngdahl, P. Nardi, U.S. Pat. No. 5,099,052 Mar. 24, 1992]:

The material, which was poorly described, suggests the formation of a trianionic hexacoordinated monomer using a diol reactant.

In all instances, the above cited studies teach only the synthesis of mono or dianionic silicates, monoanionic and trianionic aluminates and one example of a dimeric aluminate species, all based on simple mono or difunctional alcohols (diols). In all instances, the counterion is a group Ia or IIa metal. In all instances, the products are crystalline and do not offer useful viscoelastic properties necessary for forming useful shapes.

In no instance does the prior art teach a commercially viable preparation of processable polymers containing mixed anionic/neutral monomer units in the polymer backbone or the use of triols or higher "ols" for the formation of double alkoxides, especially double alkoxide oligomers and polymers, and particularly from SiO$_2$, Al$_2$O$_3$ or Al(OH)$_3$. Furthermore, none of the above cited studies teach the use of nitrogen containing triols or higher "ols" as a means to stabilize the double alkoxides to reduce moisture sensitivity, improve processability and minimize carbon content when used as preceramics.

U.S. Pat. No. 2,881,198 to D. Bailey and F. O'Connor taught that reacting silica with a catalytic amount of alkali metal hydroxide under conditions that remove water by distillation or azeotrope (often under pressure) leads to the synthesis of monomeric, neutral alkoxy silanes. However, the disclosed reaction was extremely slow, requiring days to complete. Furthermore, the yields obtained were only 50–78%, as the alkali base catalyst eventually reacted with the SiO$_2$ to produce alkali silicate byproducts.

Fry appeared to teach that silicic acid will react with a large excess of triethanolamine (TEA) to produce water and what was described as a "more or less nondescript silatrane material". Although the reaction which accompanied this disclosure incorrectly characterized the formula for silicic acid, the synthesis was predicated upon the use of TEA as the sole solvent. Also, the uncharacterized product appears to be a relatively low molecular weight species. See Frye et al., "Pentacoordinate Silicon Compounds. V. Novel Silatrane Compounds," J. Am. Chem. Soc. (1971) 93, 6805–6811.

Struchkov et al. [V. E. Shklover, Yu. T. Struchkov, M. G. Voronkov, Z. A. Ovchinnikova, V. P. Baryshok, "Crystal and Molecular Structure of the Unusual Alumatrane Complex: [Al(OCH$_2$CH$_2$)$_3$N]$_4$.3HOCH(CH$_3$)$_2$.0.5C$_6$H$_6$," Dokl. Akad. Nauk SSR (1984) 227, 1185-9. Chem. Abstracts, (1984) 102: 37181k.], teach the synthesis of [Al(TEA)]$_4$.3HOCH(CH$_3$)$_2$.0.5C$_6$H$_6$, by reaction of TEA with Al(O-Pr$^i$)$_3$ in benzene. The product is not solvent free which will affect its properties (e.g. benzene is toxic, it causes leukemia) and was not made from Al$_2$O$_3$ or Al(OH)$_3$. More recently, work by Verkade et al [Inorg. Chem. (1993) 32, 2711] confirms the Struckhov synthesis. Neither of these works describe the synthesis of anionic compounds or anionic/neutral oligomers and polymers.

SUMMARY OF THE INVENTION

It is the object of this invention to provide anionic and mixed neutral/anionic polymetallooxanes of varying molecular weights so as to be classifiable as monomers, oligomers, and polymers. It is a particular object of the present invention to provide such compounds with high molecular weights.

A further object is to make volatile versions of the claimed compounds.

A still further object of this invention is to provide a method of making the claimed compounds.

A yet further object is to provide a method of making anionic and mixed anionic/neutral polymetallooxanes from polyalkoxy, aryloxy and alkoxyaryloxy polyol ligands.

Still another object is to use polyol ligands containing nitrogen, polyolamines.

An additional object of the present invention is to provide a method of making ceramic materials having controlled ceramic yield, stoichiometry, phase, microstructure, shape, and surface area by using the polymetallooxane compounds of the instant invention as ceramic precursors or preceramic materials.

Other objects of the invention include providing methods of making ceramic and polymer fibers, fine or monodispersed powders, coatings, porous articles such as ceramic foams, filters, membranes and sensors, and compression-molded and injection molded articles using, inter alia, the preceramic polymers as provided herein.

Still other objects of the present invention include methods of using the polymetallooxane polymers of the invention as binders, as adhesives, in infiltration applications (as in wood preservation and for woven polymer or ceramic fiber preforms), and in matrix and composite materials.

Additional features of the invention will be set forth in the description which follows and will become apparent to those skilled in the art on examination of the following, or may be learned by practice of the invention.

Table 1. Peak positions (m/e) observed in mass spectrometry of spinel precursor with relative intensities. Analysis conducted using fast atom bombardment of vacuum dried sample (24 h, 225° C.).

Table 2. NMR peak positions and tentative assignments of spinel precursor. a. Sample dissolved in $CDCl_3$. b. Sample dissolved in $CD_2Cl_2$.

Thus, the present invention pertains to an ionic or mixed ionic/neutral polymetallooxane comprising the moiety:

wherein $M^1$ is selected from the group consisting of trivalent or tetravalent B, Al, Ga or In, or tetravalent, pentavalent, or hexavalent Si, Ge, Sn, Pb, Ti, Zr, or Hf; n is 2, 3 or 4 when $M^1$ is B, Al, Ga or In; and n is 3, 4, 5, or 6 when $M^1$ is Si, Ge, Sn, Pb, Ti, Zr, or Hf;

$R^1$ and $R^2$ are independently selected from the group consisting of H, OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane, or combinations thereof;

O' is bonded to $M^1$, $M^2$ or H wherein $M^2$ is selected from the group consisting of Si, Ge, Sn, Pb, B, Al, Ga, In, Ti, Zr, and Hf, an ammonium or phosphonium species, or a Group Ia or IIa metal of the Periodic Table;

wherein when one O' is bonded to $M^1$, n is 2 or 3 when $M^1$ is B, Al, Ga, or In and at least one O' is bonded to $M^2$; wherein when two O' are bonded to $M^1$, n is 2 when $M^1$ is B, Al, Ga or In; wherein when one O' is bonded to $M^1$, n is 3, 4, or 5 when $M^1$ is Si, Ge, Sn, Pb, Ti, Zr, or Hf, and at least one O' is bonded to $M^2$; and wherein when two O' are bonded to $M^1$, and $M^1$ is Si, Ge, Sn, Pb, Ti, Zr, or Hf, n is 3 or 4 and at least one O' is bonded to $M^2$; and $R^3$ is independently selected from the group consisting of $(CR_2)_y$, $(CR_2CR_2)_yN(CR_2)_y$, $(CR_2CR_2)_yNR(CR_2)_y$, $[(CR_2CR_2)_yO]_y$—$(CR_2)_y$, and combinations thereof wherein R is selected from the group consisting of H, OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane, or combinations thereof, where y is a number from 1 to 10; and wherein said polymetallooxane contains at least one $M^2$. More broadly, $R^3$ is an organic linking group selected from optionally substituted $C_{1-10}$ alkylene, $C_{4-8}$ cycloalkylene, $C_{1-10}$ alkylene or $C_{4-8}$ cycloalkylene containing one or more interspersed heteroatoms of nitrogen, sulfur, or phosphorous, said optional substituents selected from OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, and $C_{1-10}$ alkylsiloxane.

Also described is a polymetallooxane material containing the heterocyclic moiety:

wherein $Q^+$ is a counterion when M is a charged species, M is a metal selected from the group consisting of B, Al, Ga, In, Si, Ge, Sn, Pb, Ti, Zr, and Hf; wherein p may be 0, 1, 2, or 3; wherein when M is B, Al, Ga, or In, p is 0 or 1, thus corresponding to a neutral tricoordinate or anionic tetracoordinate Group IIIa polymetallooxane moiety;

wherein when M is Si, Ge, Sn, Pb, Ti, Zr, or Hf, p is 1, 2, or 3 thus corresponding to a neutral tetracoordinate or anionic pentacoordinate or hexacoordinate Group IVa or Group IVb polymetallooxane moiety; wherein $Q^+$ is an alkali metal cation, alkaline earth metal cation, an ammonium ion corresponding to the formula $R_4N^+$, or a phosphonium ion corresponding to the formula $R_4P^+$, where each R is independently selected from the group consisting of H, OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkysilane, $C_{1-10}$ alkylsiloxane, and combinations thereof; and wherein the number of such ionic or mixed ionic/neutral polymetallooxane moieties in said polymetallooxane ranges from 1 to about 150.

Upon exposure to elevated temperature, radiation or radical sources sufficient to cause pyrolysis, the claimed material will serve as a ceramic precursor or preceramic and will generally produce a ceramic material in commercially feasible yields.

Also described is a method of producing the claimed polymetallooxane by reacting an aluminoxy or siloxy or other metaloxy containing material together with an amine and a polyol, a polyolamine, or a polyolamine/group Ia or polyolamine/group IIa, or a polyol/amine/group Ia or a polyol/amine/group IIa mixture and heating the resulting mixture to a temperature sufficient to remove substantially all water produced during the reaction and recovering the polymetallooxane produced.

DESCRIPTION OF PREFERRED EMBODIMENTS

In the preparation of the polymetallooxanes described herein, compounds having the functional moieties M—O—H, M—O—M, M=O, and M—O—M' moieties may be used as starting reactants. M and M' may be selected from the group consisting of B, Al, Ga, In, Si, Ge, Sn, Pb, Ti, Zr or Hf. Preferably the starting reactant will contain Al or/and Si and, most preferably, in the form of aluminoxy or siloxy functional groups. Suitable aluminoxy or siloxy containing materials that may be used are any sands, ores, and the like, that would provide aluminum hydroxide, alumina, silica or other aluminosilicate materials. The metaloxy compound may optionally contain metal atoms other than those from groups IIIa, IVa, and IVb. All that is desired is that the aluminoxy ore or the siloxy or metaloxy containing material be reactive with the amine/polyol, polyolamine, polyolamine/group I or polyolamine/group II, polyol/amine/group I or polyol/amine/group II mixtures described below to produce the desired polymeric polymetallooxane. Simple oxides and hydroxides and their hydrates are suitable, for example. The term "metaloxy compound" as used herein is inclusive of all such compounds.

The term "polymetallooxane" as used herein is intended to encompass both low and high molecular weight structures, such that monomers, oligomers and high molecular weight polymers are within the scope of the claimed polymetallooxane. The M atom may be present in the desired materials in branched moieties or heterocyclic moieties or both. The claimed polymetallooxane may contain but one M atom or, in the case of silicon, two or more, preferably three or more silicon atoms. Mixed polymetallooxanes, for example those containing both aluminum and silicon are also contemplated, as are polymetallooxanes containing these and other M' moieties and other metals from the periodic table, particularly the metals of Groups Ia and IIa. Most preferably, the polymetallooxanes contain 2 or more, more preferably 3 or more metal atoms from Groups IIIa, IVa, or IVb.

The amines that will be preferably utilized in the present invention can be selected from a wide variety of nitrogen containing materials. Preferably, however, the amine utilized herein will have a high boiling point. Most preferably, the amine utilized herein will be a high boiling polyolamine. Alternatively, high boiling amines and polyols can be used in combination. Of these, polyamines and polyols are preferable. Di- and trisubstituted amines and polyamines are preferred because they provide a higher base strength. For example, simple $C_2$ to $C_{10}$ amines and polyamines such as primary, secondary and tertiary amines, where the substituents are preferably methyl, ethyl or lower alkyl groups may be utilized with polyols. The amine substituents can be essentially any other organic radical so long as they do not interfere with the desired reaction. Hydrogen, benzyl, alkoxyalkyl, hydroxyalkyl, and the like are illustrative, but not limiting examples. Divalent organic groups, such as alkylene or substituted-alkylene, e.g. oxyalkylene or poly-(oxyalkylene), or less desirably, arylene, alkarylene or substituted arylene can also be used. Unsaturated groups, e.g. alkylene groups such as —CH=CH— or —CH=C(R)— can also be used wherein R may be one of the substituent groups discussed immediately above. Other possible R groups include cyclic or aromatic groups; one type of useful amine, for instance is represented by the formula:

HO—[(CH$_2$)$_x$—NR$^1$R$^2$]

where x is 1 to 3 and $R^1$ and $R^2$ are as discussed immediately above. Other examples of suitable polyamines that can be used in conjunction with polyols include diethylenetriamine, triethylenetetramine, tetraethylenepentamine, and polyethylene imine. Dialkanolamines, of the general formula RN(R—OH)$_2$, and trialkanolamines of the general formula N(R—OH)$_3$, and polyamines of the general formula:

XCH$_2$—(CH)$_x$—[(CH$_2$)$_z$—NR$^1$R$^2$]
|
X where X is H or OH and such that the formula contains at least two OH, x and z are independently 1–6, at least two of said at least two OH are in 1,2- or 1,3-relationship to each other, $R^1$ and $R^2$ are as discussed immediately above, are also useful. Cyclic amines such as morpholine or piperazine and their derivatives may also be used. Polyoxyalkylated amines and substituted amines are also useful.

Some specific examples of suitable amines that may be used with or without polyols are dimethylethanolamine, dimethylpropanolamine, dimethylisopropanolamine, dimethylbutanolamine, dimethylisobutanolamine, dimethyltert-butanolamine, diethylethanolamine, diethylpropanolamine, diethylisopropanolamine, methylethanolamine, N-benzylethanolamine, diethanolamine, triethanolamine, triisopropanolamine, tripropanolamine, triisobutanolamine, 2-amino-1,3-propandiol, 1-amino-2,3-propandiol, 1-amino-2,3-butandiol, 2-amino-1,3-butandiol, 2-amino-1,4-butandiol, 1-amino-2,3-cyclopentandiol, 1-amino-2,3-cyclohexandiol, 1-amino-2,3-dihydroxybenzene, 4-amino-2,3-dihydroxytoluene, and 5-amino-2,3-dihydroxytoluene. This list is illustrative and not limiting.

The most preferred polyamines are triethanolamine (TEA) and triisopropanolamine. The most preferred polyol/amine mixtures are ethylene glycol/triethylenetetramine and glycerol/triethylenetetramine. Any and all of these systems can be used in the absence of or in the presence of group Ia or IIa metal oxides or hydroxides.

It is also most preferred that the reaction to produce the claimed polymetallooxane polymeric materials described herein take place in the presence of reactive solvents such as polyols which may be necessary to effect reaction.

Some specific examples of polyols that can be used with these amines include:

Ethane-1,2 diol (ethylene glycol), 1,2-propanediol, 1,3-propanediol, 1,2-butanediol, 1,3-butanediol, 1,2-cyclopentanediol, 1,2-cyclohexanediol, 1-phenyl-1,2-ethanediol, 1-phenyl-1,2-propanediol, 1-phenyl-1,3-propanediol, 1,2,3-propanetriol (glycerol), polyvinylalcohols of any molecular weight and degree of hydrolysis, and mixtures thereof. The enol form of 2,4-pentandione can also be used. Also useful are the polyoxyalkylene polyether polyols with functionalities of from 2 to about 8 prepared by oxyalkylating a polyhydric initiator with an alkylene oxide in the presence of a suitable oxyalkylation catalyst, for example an alkali metal or alkaline earth metal oxide or hydroxide, alkali metal alkoxide, or double metal cyanide-type catalyst. Suitable initiators are, for example, any of the amines and/or glycols described previously, as well as hydroquinone, resorcinol, 4,4'-dihydroxybiphenyl, 4,4'-dihydroxydiphenylmethane (bisphenol F) and the other bisphenols, trimethylolpropane, trimethylolethane, neopentyl glycol, pentaerythritol, α-methylglucoside, glucose, sorbitol, sucrose, and the like. Preferred alkylene oxides are ethylene oxide (oxirane), propylene oxide (methyloxirane), 1,2- and 2,3-butylene oxide, oxetane, and tetrahydrofuran. The molecular weight of the polyoxyalkylene polyether polyols may be selected for the desired effect. In general, equivalent weights of from about 100 to about 10,000, more preferably 100 to about 1000, and most preferably about 100 to about 500 are useful.

The most preferred reactive solvents are the 1,2 and 1,3 diols. Of these, ethylene glycol is most preferred.

It is also desirable to utilize non-reactive solvents, such as oxygen containing solvents which are widely available as ether-containing solvents. Preferred non-reactive solvents are monoalkyl or dialkylethers of ethylene glycol, diethylene glycol, triethylene glycol, or tetraethylene glycol. The alkyl group preferably contains from 1 to 4 carbon atoms. the use of such non-reactive solvents may be advantageous with respect to the high cost and low availability of some reactive solvents, particularly some preferred diols, such as diethyl tartrate for example. Illustrative examples of suitable non-reactive solvents include the crown ethers, diethoxydiethylene glycol or polyethers such as the polyethylene glycols to molecular weights of up to about 2000.

Exemplary materials are Cellosolve (trademark of Union Carbide for monoethyl ether of ethylene glycol), methyl Cellosolve, butyl Cellosolve, isobutyl Cellosolve, hexyl Cellosolve, Carbitol (trademark of Union Carbide for monomethyl ether of diethylene glycol), butyl Carbitol, hexyl Carbitol, monobutyl ether of propylene glycol, monopropyl ether of propylene glycol, monomethyl ether of propylene glycol, monomethyl ether of dipropylene glycol, polypropylene glycol to molecular weights of about 2000, and the like.

The reaction temperature to produce the claimed polymers can vary depending on the reagents utilized. An operative consideration is that as the reaction proceeds, water must be removed completely, preferably by distillation, otherwise crystalline zeolitic products will obtain [Bibby, D. M.; Dale, M. P., Nature, 1985, 317, 157–158. b. van Erp, W. A.; Kouwenhoven, H. W.; Nanne, J. M.; Zeolites, 1987, 7, 286–88. Herreros, B.; Carr, S. W.; Klinowski, J.; Science, 1994, 263, 1585–1587.]. Generally, the temperature and pressure will be adjusted so that the polyolamine or polyol/amine compounds will remain in the liquid phase, while the water will be removed.

Accordingly therefore, when the reaction is operated at atmospheric pressure, the temperature will range from approximately 100° C. to 250° C. Alternately, if an azeotropic mixture is utilized and the reaction is run at atmospheric pressure, the temperature is decreased since azeotropes generally boil at lower temperatures. Correspondingly, if the pressure is less than atmospheric pressure, that is, if a partial vacuum is applied, the reaction temperature necessary to remove water will likewise be less. If the pressure is greater than atmospheric, then the reaction temperature required to remove water will be higher.

In preparming the polymetallooxanes, a di- or polyhydroxyl functional reactant is necessary. Further necessary is an amino group-containing compound. If the polyhydroxyl functional reactant is a polyamine, such as triethanolamine or triisopropanolamine, then this hydroxy functional reactant also contains the necessary amino functionality to allow the reaction to proceed. If, however, the hydroxyl functional reactant is a simple glycol, polyoxyalkylene glycol or polyol, or the like, then it is necessary to additionally employ a polyolamine or organic amine, the latter two compounds preferably in less than stoichiometric amount based on the number of metal centers. Without wishing to be bound by theory, it is believed that the amino group acts catalytically to promote the reaction of the hydroxyl groups with the metaloxy compound.

When a glycol or polyol is the principle reactant and the amine or polyolamine are used in less than stoichiometric amount, the polymetallooxane products generally contain multiple metal centers connected with —O—R—O— linkages, these linkages derived from the glycol or polyol. When tri- or higher functionality polyols are utilized, for example glycerol, a branched —O—R(—O—)—O— center may be created. Some residues of polyolamine may also be incorporated into the polymetallooxane, the amount to some degree dependent on the amount of polyolamine utilized.

When stoichiometric or higher than stoichiometric amounts of a polyolamine are utilized, the product may contain substantial quantities of polyolamine residues, or even all polyolamine residues. The amount of such residues in the product can be controlled, to a first approximation, by removing a greater amount of glycol from the reaction mixture when mixtures of glycol and alkanolamine are used. For reasons which are not totally clear, it appears that the metal atoms of the polymetallooxane have a higher affinity for polyolamine derived moieties than glycol or polyol derived moieties, and that an equilibrium between these species exists, which can be shifted by removal of glycol, for example by distillation.

The metal, M, should be selected from the elements exemplified, in particular the metals of groups IIIa, IVa, and IVb of the periodic table. However, it is further possible to add to the mixture of metaloxy reactants other metals whose mixed polymetallooxanes may be useful in the formation of coatings, ceramics, glasses, etc. Among the additional metals which may be added, particularly in the form of their oxides, hydroxides or hydrated forms of the latter, are the group Ia and IIa elements which are commonly found in many natural silicates, aluminates, and aluminosilicates. While these elements may be added in any amount, it is often preferable to add them in such amounts that the finished polymetallooxane product contains the metals in the same ratio as known glasses or ceramics. An example of the latter is spinel, $MgAl_2O_4$, containing magnesium and aluminum in a 1:2 ratio.

Additional metals which may be utilized to form mixed polymetallooxanes with one or more of the group IIIa, IVa, or IVb elements are the lanthanide and actinide metals, the former particularly useful in silicon polymetallooxanes, and the remaining transition metals of the first, second, and third transition metal series.

When silicon is the metal M, the polymetallooxanes are preferably polymeric, i.e., have three or more silicon atoms linked by —O—R—O— linkages. The —O—R—O— linkage may be glycol or polyol derived, or may be derived from an alkanolamine, in which case the R group will contain a nitrogen atom. Some polyamine linkages may be cyclic, i.e., attached to the same silicon atom. Cyclic linkages are also important with other polymetallooxanes. However, the claimed process of the invention may be used not only to prepare polymeric polymetallooxanes of silicon, but dimeric and monomeric species, both neutral, anionic, and mixed neutral/anionic as well.

The polymetallooxanes of the subject invention may be composed of entirely neutral species. Thus, when the metal M is aluminum, —O—R—O— linkages may be created, with no more than three such linkages or other linkages (e.g., —O—R, such as methoxy, ethoxy) attached to any given aluminum atom. The aluminum atom will thus be a trivalent, uncharged, neutral species. With the four-valent metals, for example silicon and titanium, all neutral polymetallooxanes may be prepared which contain linear or cyclic —O—R—O— linkages with no more and no less than four of such linkages (together with other linkages such as —O—R or —O—Si(OR)$_3$) attached to the metal atom. Thus, these metal centers, being tetravalent, will also be neutral centers.

However, it is also possible, by suitable choice of reactants, to prepare polymetallooxanes containing tetravalent aluminum or other group IIIa elements, or pentavalent silicon, titanium, or other group IVa or IVb elements. In such cases, the normally trivalent group IIIa metal centers, being tetravalent, will be anionic, as will also be the pentavalent or hexavalent normally tetravalent centers associated with the group IVa and IVb elements. If is further possible to prepare polymetallooxanes which have both neutral and anonic centers. These centers may be from the same metal M, or may be from mixed metals, i.e. aluminum and silicon.

If the polymetallooxane monomers, oligomers and polymers that are obtained according to the claimed invention contain a heterocyclic moiety, it is preferred that moiety comprise the structure:

wherein M is B, Al, Ga, In, Si, Ge, Sn, Pb, Ti, Zr, or Hf; wherein when M is B, Al, Ga, In, p is 0 or 1; and when M is Si, Ge, Sn, Pb, Ti, Zr, or Hf, p is 1 or 2; when M is B, Al, Ga, In and p is 1, Q$^+$ is a group Ia, group IIa or ammonium or phosphonium moiety; and when M is Si, Ge, Sn, Pb, Ti, Zr, or Hf, p is 2, Q$^+$ is a group Ia, group IIa or ammonium or phosphonium moiety, preferably those corresponding to the formulae R$_4$N$^+$ or R$_4$P$^+$ where R is independently selected from the group consisting of H, OH, C$_{1-8}$ alkyl, C$_{1-6}$ alkoxy, C$_{2-8}$ alkenyl, C$_{6-12}$ aryl, C$_{1-8}$ hydroxyalkyl, C$_{1-8}$ thioalkyl, C$_{2-12}$ alkoxyalky, C$_{4-20}$ heteroaromatic, C$_{1-10}$ alkylsilane, C$_{1-10}$ alkylsiloxane and combinations thereof, wherein Z is the residue of an amine reactant. Note, however, that not all of the heterocycle moieties will contain a dative bond, i.e. an N—M bond.

When the polymetallooxane incorporates portions of the reactive solvent, when mixtures of glycols and polyol amine are used, for example, the glycol residues will not bond to N with the exception of hydrogen bonds. When group Ia or IIa metals are also used as coreactants, not all of the resulting polymetallooxane polyolamine ligands form dative bonds to M. An illustrative example is the partially volatile compound:

The polymetallooxanes having branched moieties may be characterized as [O—R$^1$—O]$_x$M(O—R$^2$—O)$_y$]M$^2$ where M is B, Al, Ga, In, Ti, Zr, Hf, Si, Ge, Sn, or Pb or a Group Ia or IIa metal; R$^1$ and R$^2$ are independently selected from the group consisting of C$_{1-8}$ alkyl, C$_{1-6}$ alkoxy, C$_{2-8}$ alkenyl, C$_{6-12}$ aryl, C$_{1-8}$ hydroxyalkyl, C$_{1-8}$ thioalkyl, C$_{2-12}$ alkoxyalky, C$_{4-20}$ heteroaromatic, C$_{1-10}$ alkylsilane, C$_{1-10}$ alkylsiloxane and combinations thereof; M$^2$ is selected from the group consisting of B, Al, Ga, In, Ti, Zr, Hf, Si, Ge, Sn, Pb, or the Group Ia or IIa metals or the residue of an amine or phosphonium reactant; and x and y may be the same or different and are numbers from 1 to 10, preferably 1–4, and more preferably 1–3. The above structure represents one example, still another example is:

The branched double alkoxides, as exemplified by the above structures, can vary in molecular weight as a consequence of several parameters including the polyolamine used, the use of reactive solvents, the temperature, the concentration and the presence of group Ia or IIa metals. At low concentrations of polyolamines, the degree of crosslinking in the polymetallooxanes will be decreased. Also the use of simpler diols, such as ethylene glycol, favors lower crosslink density. Consider for example:

The use of triols and higher functionality polyols, such as polyvinyl alcohol, will generally increase the degree of crosslinking as illustrated above. Higher temperatures will promote increased crosslinking through the reaction of dangling R—OH of the branches which leads to higher viscosities in the resulting polymeric polymetallooxane as illustrated by:

Higher concentrations of amines will also promote the above reaction. At the other extreme, it is possible to prepare oligomeric species containing only ionic interactions:

Such anionic species can be volatile without the instability, intractability or toxicity of the related $Al(OCH_3)_3$ compound. Furthermore, there is no precedent for their formation. The ceramic yield for this compound is much higher than for the related $Mg[Al(OPr^i)_4]_2$ compound because it has a 40% lower carbon content (10 carbons less per dimer) with two extra nitrogens. Unlike carbon, nitrogen is normally not incorporated as a contaminant.

It is also to be appreciated that the polymetallooxane monomers, oligomers and polymers that are obtained can contain various cyclic moieties wherein the number of members of the ring can range from 5 to 9. An illustrative example is:

Another example with both anionic (Al) and neutral (Si) components is:

After the polymeric materials are obtained, they may be heated to a temperature sufficient to obtain pyrolysis to generate the desired end products such as glasses or ceramics.

Most preferably, polymetallooxanes prepared by the synthesis of anionic or mixed anionic/neutral polyolamine aluminates and aluminosilicates from aluminum oxides and hydroxides [$Al_2O_3$, AlO(OH), and Al(OH)$_3$], and $SiO_2$, or mixtures of these oxides with high boiling polyolamines such as triethanolamine and a reactive solvent such as ethylene glycol is contemplated. Thus, the instant case is concerned with a method of dissolving aluminum oxides and hydroxides [$Al_2O_3$, AlO(OH), and Al(OH)$_3$], or $SiO_2$, or mixtures of these oxides (in any molar ratio) in the presence or absence of group Ia or IIa hydroxides or oxides in ethylene glycol (or any other 1,2 or 1,3 diol or polyol or polyolamine, or mixtures thereof) with removal of product water in the presence of stoichiometric or catalytic amounts of a high boiling amine, oligoamine or polyamine. Such compounds, as well as other polymetallooxanes, may be prepared using 1,4-, 1,5-, or 1,6-glycols or other glycols where the hydroxyl groups are more widely separated than in 1,2- and 1,3-glycols, but only when used in conjunction with the latter.

The products of these reactions with catalytic amounts of amine are neutral, branched alkoxy polymetallooxane complexes or polymers, as are generally also the products prepared from stoichiometric or lesser amounts of polyolamines. In the presence of slightly less than stoichiometric or stoichiometric amounts of amine and group Ia or IIa metal ions, the products are generally either branched or heterocycle containing and anionic. While not wishing to be bound to any particular theory, it is believed that the addition of group Ia or IIa metal containing materials cause the formation of mixed anionic/neutral complexes or polymers. The rheological and chemical properties of the desired products can be controlled by the type of polyol or polyolamine present, the reaction conditions and the amount and type of the polyol, amine or polyamine or polyolamine added as discussed above.

For example, if a mixture of five equivalents of TEA is reacted with two equivalents of Al(OH)$_3$ and one equivalent of MgO, as described below, followed by vacuum evaporation of ethylene glycol solvent following complete dissolution of the oxides, then a viscoelastic product is obtained.

This product is suitable for melt coating and spinning applications. The properties of the product may range from a high temperature liquid crystalline polymer (e.g. where catechol and/or hydroquinone are/is added as a reactive diol) to a flexible, scratch-resistant polymer/ceramic composite.

In another example, if a mixture of three equivalents of TEA is reacted with two equivalents of Al(OH)$_3$ and one equivalent of MgO, as described below, followed by partial vacuum evaporation of ethylene glycol solvent following complete dissolution of the oxides, then a very viscous product is obtained. This product is also suitable for melt coating and spinning applications. However, if all of the ethylene glycol is removed, then the product can be a high melting viscoelastic polymer with similar properties; but with time or the aid of nucleating sites, the product crystallizes.

Still a third product can be made if a mixture of three equivalents of TEA is reacted with two equivalents of Al(OH)$_3$ and one equivalent of MgO as described below with complete vacuum evaporation of ethylene glycol solvent followed by higher temperature vacuum removal of small amounts of TEA. The resulting material is a highly crosslinked polymer as illustrated above; however, it will redissolve in alcohol solvents to produce a processable polymer.

It has also been found that the claimed polymeric polymetallooxanes are particularly advantageous when used as ceramic precursors or preceramics. Hydrolysis with subsequent or simultaneous heating of the above polymetallooxane polymers, especially or the Si/Al materials could provide zeolitic materials, aerogels, or xerogels depending on the workup. Pyrolysis of 2:1 mixtures of Al:Mg double alkoxides produced as described herein will provide spinel powders, coatings or high surface area membranes at temperatures as low as 500°–800° C. depending on the processing conditions and degree of crystallinity desired.

Low solvent content samples can be melt spun at temperatures of 160°–230° C. Alternately, a volatile solvent such as methanol or dichloromethane can be added to permit spin and/or tape casting or dry spinning of fibers. These precursors are suitable for spinning fibers that are precursors to spinel, mullite, and/or cordierite. Dissolution in methanol or ethanol provides solutions that can be flame spray pyrolyzed to produce large quantities of high surface area, low porosity, nanosized powders of alumina, titania, mullite, spinel, group Ia and group IIa aluminosilicates. The bulk polymers, following pyrolysis in air or oxygen, provide high surface area particles that can be nitrided in flowing NH$_3$.

Polymetallooxane as used herein is intended to describe compounds which contain multiple metal-oxygen-carbon bonds per metal center. Preferably such compounds will have from three to six such bonds. In the instances where an oligomer or polymer is formed and some of the metal centers are anionic, the counterions are group Ia or IIa metals or ammonium or phosphonium species. The nitrogen of the amine and/or ammonium species associated with the anionic metal centers is not required to bond to the metal center, although, this may occur for some specific amines and/or metals.

For example, if triethanolamine is used as reactant, it can bridge metal centers or it can chelate metal centers. It can also chelate and bridge either by forming alkoxide bonds or through Lewis base-Lewis acid interactions with other metal centers. In the compound, [Al(TEA)]$_4$, the $^{27}$Al NMR (in CD$_2$Cl$_2$) shows three broad peaks: 64.4 (major, tetracoordinated), 29.0 (trace, pentacoordinated), and 5.1 ppm (major, hexacoordinated). The peak at 64.4 is associated with a tetracoordinated Al wherein either a dative Al—N bond or a Lewis acid/Lewis base pair occupies the fourth coordination site. In the compound HMgAl$_2$ (TEA)$_3$ $^{27}$Al NMR [in CD$_2$Cl$_2$] shows a major peak at 66.3 (tetracoordinated) and a minor peak at 5.1 ppm (trace). In this instance, no dative Al—N bond is expected and none is apparent. The fourth coordination site is taken up by the bridging TEA.

Thus, the polymetallooxanes of the instant invention are not classified as alumatranes since the dative bonds between N and M are optional rather than mandatory.

"High molecular weight" polymers as provided herein are polymers that have an $M_n$ greater than about 10 k Da, in some cases greater than 20 k Da, and an $M_w$ greater than about 30 k Da and in some cases greater than 100 k Da. $M_n$ and $M_w$ have their standard definitions of number and weight average molecular weight respectively.

"Substantially linear" oligomers or polymers as used herein are noncyclic structures having two or more monomeric units and which are not extensively crosslinked, where the monomeric units may contain small cyclic moieties. For example, in the TEA dissolution of aluminum hydroxide, the following "substantially linear" oligomers have been identified:

n=2–5

In another example, "highly branched" oligomers or polymers are observed in the reactions of MgO and aluminum hydroxide:

A "substantially pure" ceramic material is intended to mean a ceramic material wherein the ratios of the various metal atoms correspond in an amount of at least 75% to a particular compound. For example, pyrolysis of the above compound, made by reacting three equivalents of TEA with two equivalents of Al(OH)$_3$ and one equivalent of MgO as described below followed by vacuum distilling all volatiles produces a polymer that on heating to 1000° C. in air or in oxygen for one to two hours produces a 26% ceramic yield. The resulting ceramic material is phase pure spinel, MgAl$_2$O$_4$.

A "rheologically useful" polymetallooxane polymer is defined as one which is meltable, soluble or deformable such that shapes can be formed.

It is a particularly useful aspect of the present invention that meltable, soluble, volatile, and spinnable products may be obtained, in contrast to the poorly characterized intractable polymers or crystalline materials prepared from compounds such as trialkoxyaluminum and tetraalkoxysilane. In this respect, it should be noted that when the metals M are all silicon, and triethanolamine is the polyhydroxyl compound, the molar ratio of triethanol amine to silicon should be 1.5 or less, preferably about 1:1, and the reaction should be advantageously conducted in a reactive solvent such as ethylene glycol, otherwise poorly characterized low molecular weight prcducts may be obtained.

The claimed reaction is carried out under nitrogen or air, in solution, with the solvent comprising ethylene glycol or other diol or polyol to which has been added up to two equivalents of a group I or II metal oxide or hydroxide and up to one equivalent of a high boiling amine per equivalent of metal, preferably TETA or triethanol amine.

The reaction is run so as to drive off water which is produced during the reaction process. To do this, it is preferable to create conditions wherein the reaction is run above the boiling point of water. With ethylene glycol, the preferred reaction temperature is 200° C., the boiling point of ethylene glycol. However, by using partial vacuum, it is possible to run this reaction at temperatures as low as 100° C. It is also possible to run the reaction at temperatures below 100° C. at reduced pressures, or with a solvent that can be used to remove the water by azeotrope. Thus, ethanol can also be used as solvent. Aluminum hydroxide can be dissolved with TEA in ethanol at a reaction temperature of 72° C.

The tradeoff is that at lower reaction temperatures, the kinetics of the reaction are slower and reactions may take weeks to complete. Thus, the range of reaction temperatures may be from 50°–290° C., preferably from 150°–250° C., and most preferably from 180°–230° C.

While having described the invention above listed below herein are preferred embodiments of the invention wherein all of the temperatures are in degrees Centigrade and parts are parts by weight unless otherwise indicated.

EXAMPLE 1

Preparation of the trimer, $HMgAl_2[N(CH_2CH_2O)_3]_3$

Aluminum hydroxide hydrate $(Al(OH)_3 \cdot xH_2O)$ was purchased from Aldrich Chemical Company, Inc. (Milwaukee, Wis.) and used as received (54.84 wt. % $Al_2O_3$). Triethanolamine, TEA $[N(CH_2CH_2OH)_3]$ was purchased from Aldrich, and used as received (98%). Analytical reagent grade ethylene glycol $(HOCH_2CH_2OH)$ was purchased from Mallinckrodt (Paris, KY.) and redistilled to remove $H_2O$. Ethylene glycol recovered from the reaction was redistilled and recycled into the reactions. Magnesia (MgO) was purchase from Strem Chemical, Inc. (Newburyport, Mass.) and used as received (98%).

Aluminum hydroxide hydrate powder (45.0 g, 242 mmol $Al_2O_3$), and MgO (6.2 g, 242 mmol) were suspended with 1.1 equivalents (1.1 nitrogens per metal atom) of TEA (106.2 ml, 799 mmol) in EG (≈300 ml). The solution was mechanically stirred and heated to promote reaction, by distilling off EG coincident with the reaction by-product, $H_2O$. Additional EG was added as needed to lower the viscosity of the reaction. The solution cleared after 8 h reaction, indicating complete dissolution of the oxides. Solvent EG was distilled off to concentrate the solution to approximately 200 ml. The solution solidified on cooling. Reheating to 150° C. was necessary to transfer the product from the flask.

Figure 1:
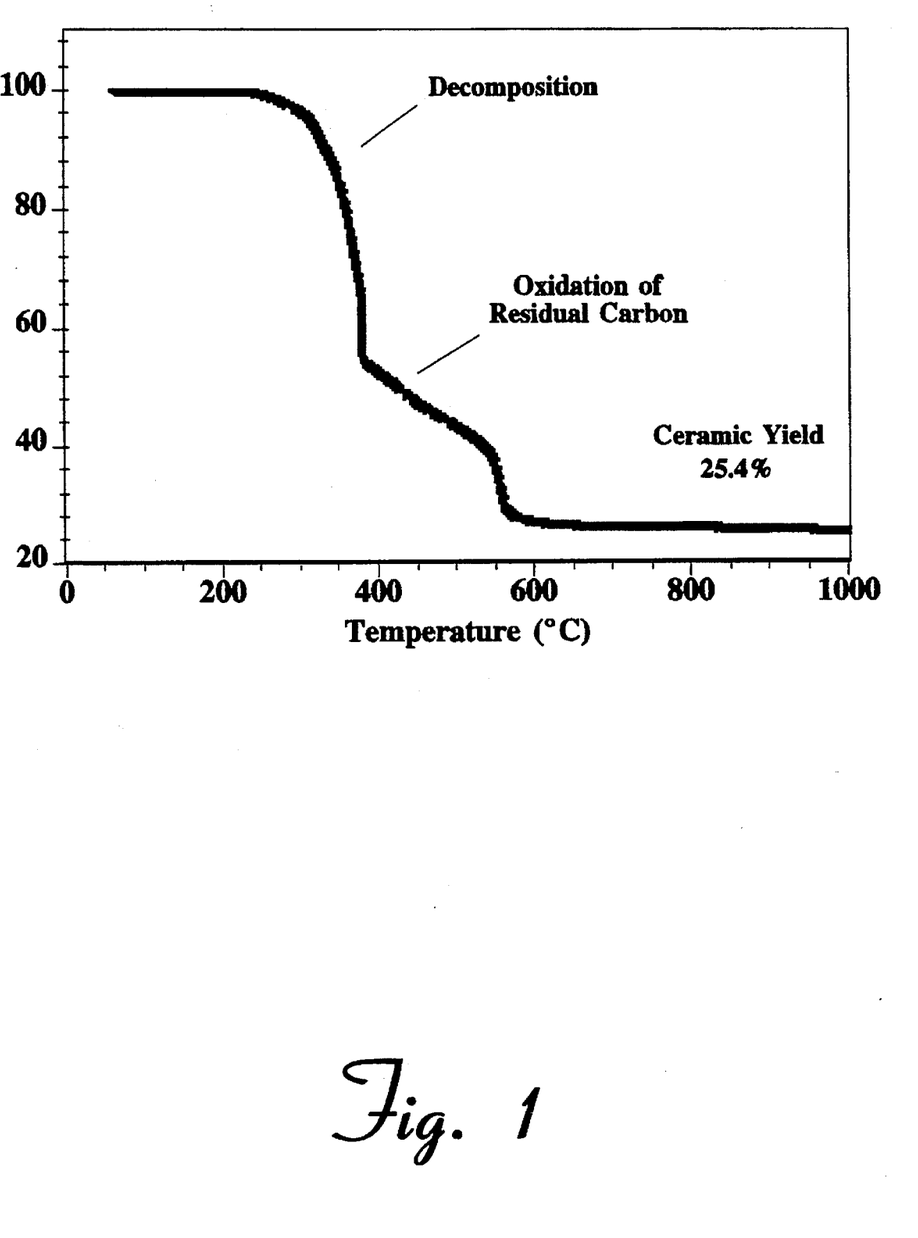
FIG. 1. TGA of spinel precursor in synthetic air. Sample was vacuum dried at 225° C. for 24 h.
Figure 2:
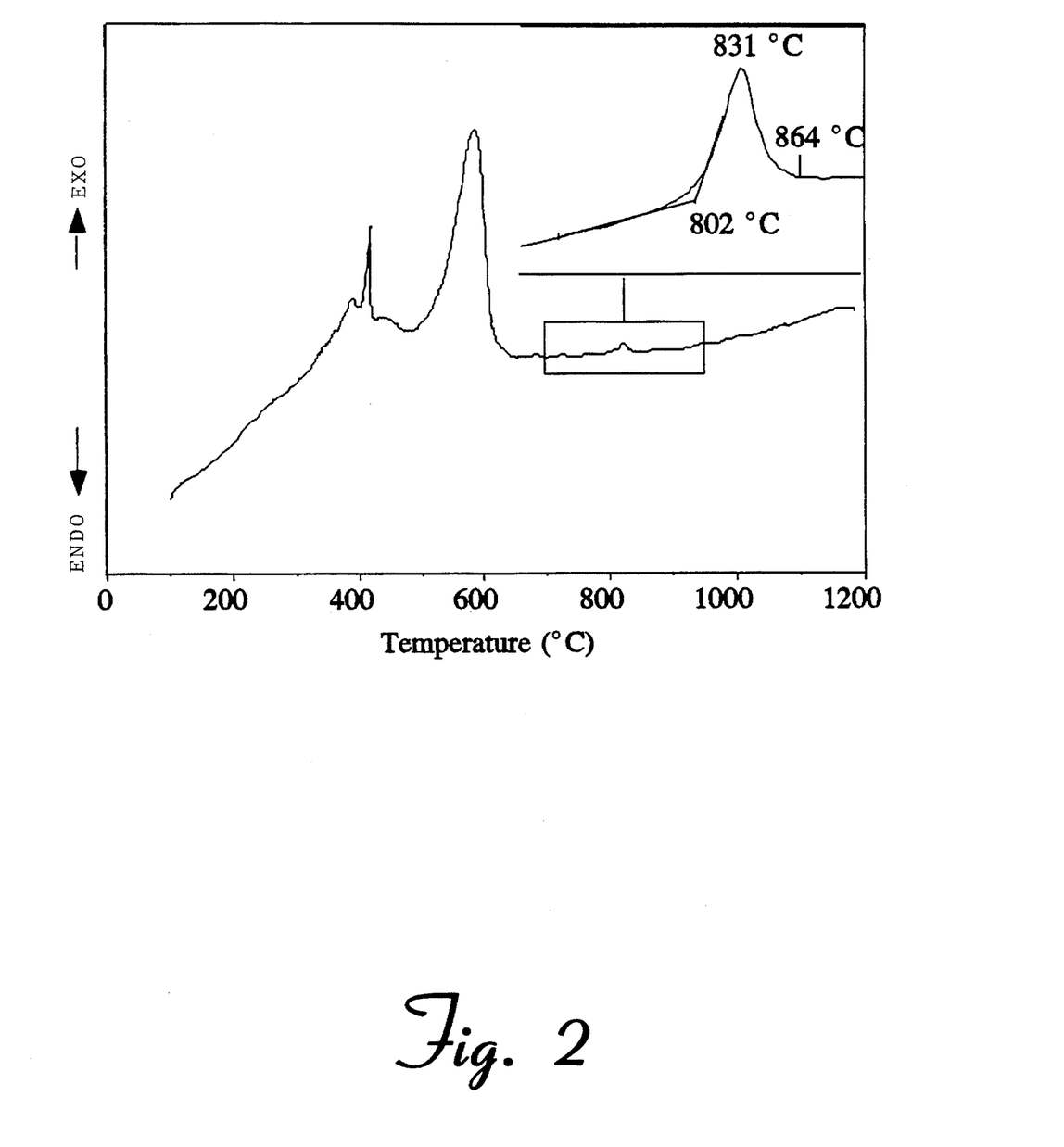
FIG. 2. DTA of spinel precursor in synthetic air. Sample was vacuum dried at 225° C. for 24 h. Inset shows crystallization of a bulk sample pyrolyzed at 400° C. (air/4 h) and then at 500° C. ($O_2$/4 h).

Small quantities (<20 ml) of precursor solution were concentrated for TGA (FIG. 1), DTA (FIG. 2), mass spectrometric analysis (Table 1) and NMR (Table 2), by heating in a 100 ml schlenk flask to 225° C. under vacuum ($10^{-2}$ Torr) for 24 h, to remove any remaining EG and excess TEA. The resulting brittle solid was then pulverized, after cooling to liquid $N_2$ temperature, with an alumina mortar and pestle to give a yellow powder. This powder was again dried under vacuum (225° C., 4 h) to minimize traces of unreacted TEA in the sample.

Figure 3:
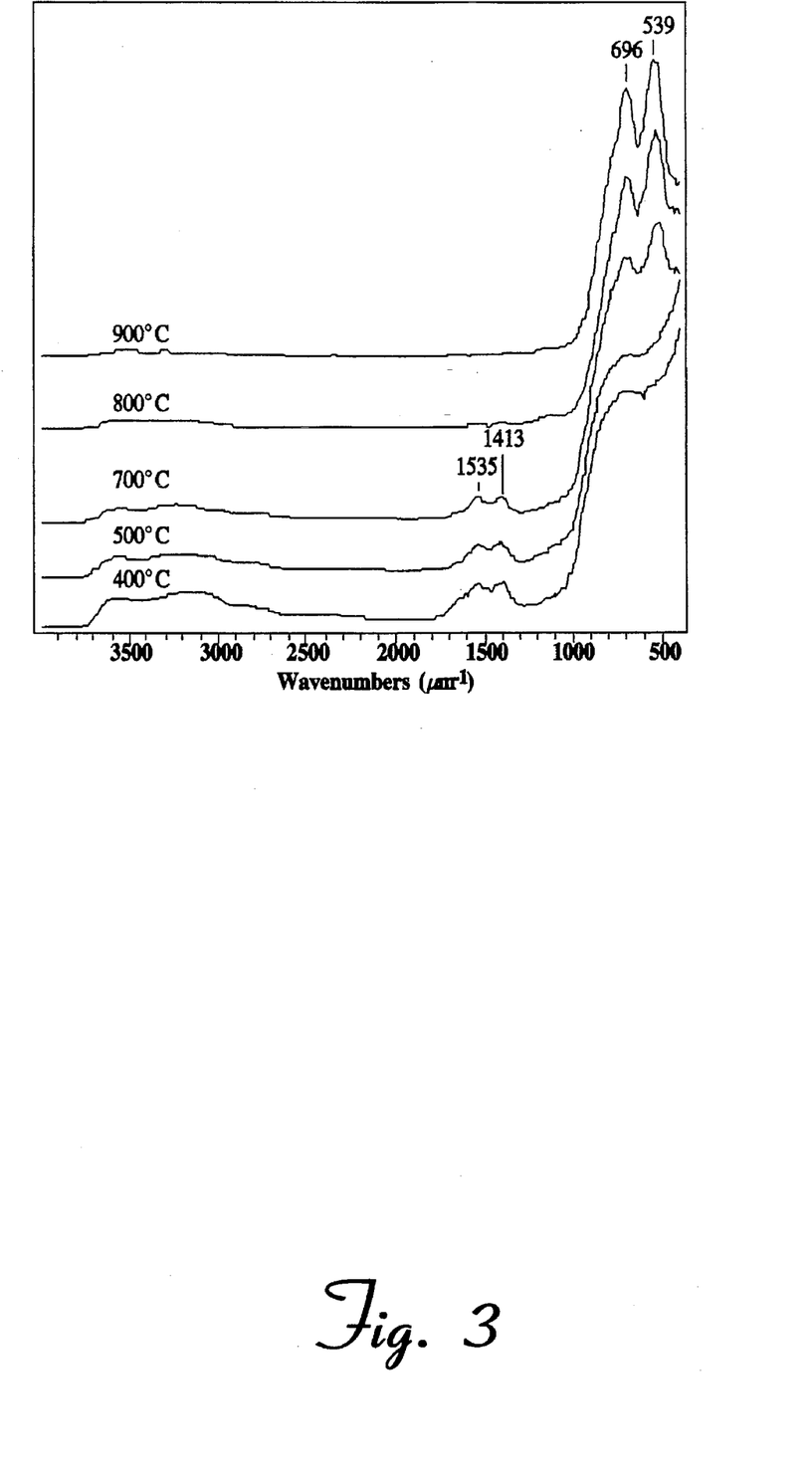
FIG. 3. DRIFT (Diffuse Reflective Infrared Fourier Transform) spectra of spinel precursor for increasing pyrolysis temperatures. All samples (except 400° C.) prepyrolyzed at 400° C. (4 h in synthetic air) and 500° C. (4 h in $O_2$). Pyrolyses at 700° C. and higher conducted for 2 h.
Figure 4:
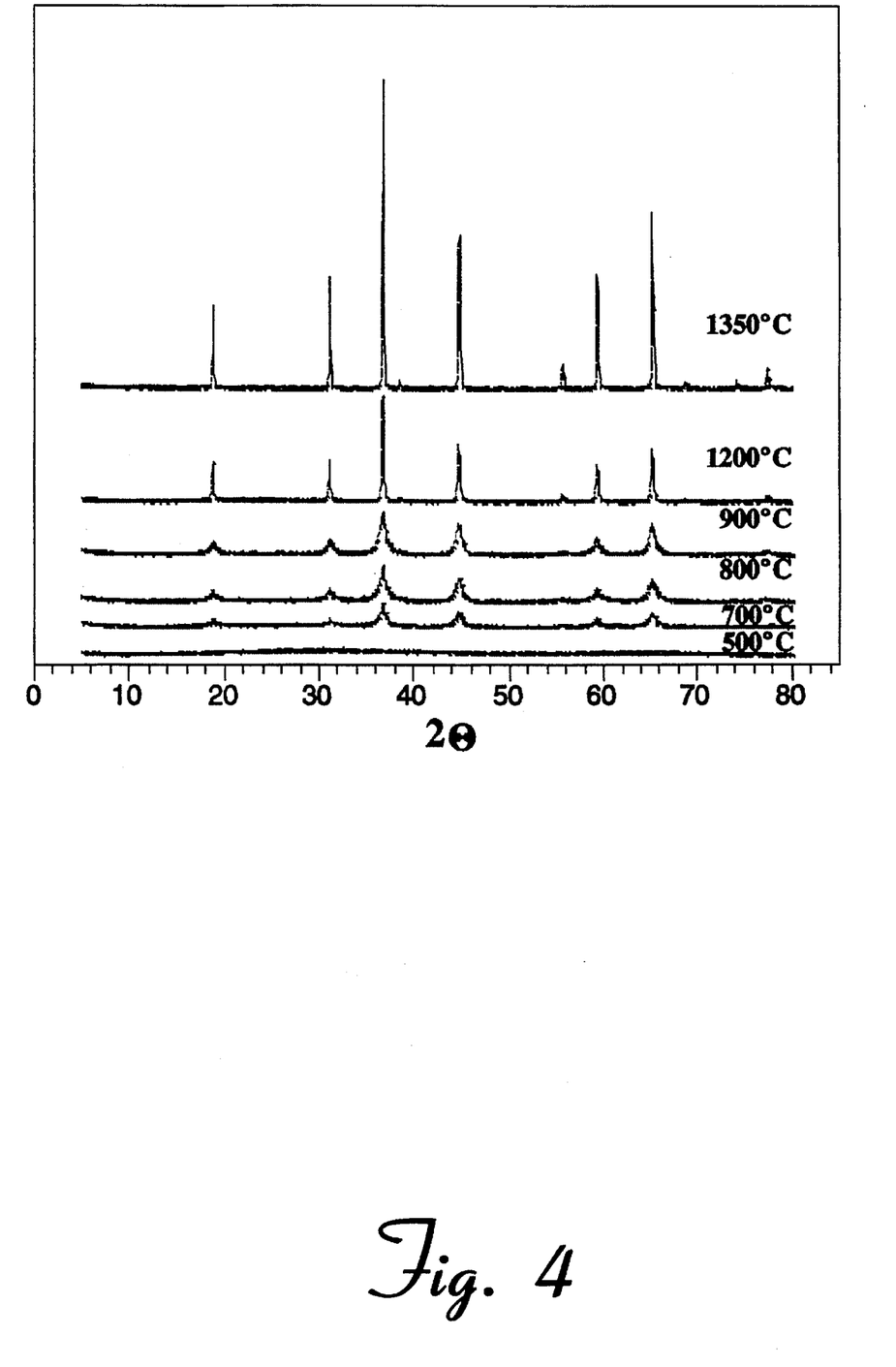
FIG. 4. Powder X-ray diffraction pattern of spinel precursor for increasing pyrolysis temperatures. All samples prepyrolyzed at 400° C. (4 h./synthetic air) and 500° C. (4 h/$O_2$). Pyrolyses at 700°–1200° C. conducted for 2 h in air, 1350° C. sample pyrolyzed 4 h in air. Peak positions are for $MgAl_2O_4$, JCPDS No. 21-1152.

Samples prepared in the same way were also used for pyrolytic studies to examine the changes that occur on the atomic scale as a consequence of the processing temperature (DRIFTS, FIG. 3) and at the microstructural level (XRD, FIG. 4).

EXAMPLE 2

Preparation of the polymer, $\{MgAl_2[N(CH_2CH_2O)_3]_3\}_x$

Magnesium hydroxide, 2.89 g $Mg(OH)_2$ (81 mmol as MgO), was suspended in 200 ml of ethylene glycol in a 500 ml flask and heated to distillation temperature. After 2 h, 15 g $Al(OH)_3$ (161 mmol as $Al_2O_3$) and 36 g TEA (242 mmol) were added. The solution was mechanically stirred and heated to promote reaction, by distilling off EG coincident with the reaction by-product, $H_2O$. The solution became clear after 2 h as all of the oxides dissolved. Solvent EG was distilled off to concentrate the solution to ≈80 ml. The solution solidified on cooling. The resulting polymer was treated as in Example 1. The yield of product was quantitative. The DTA, DRIFTS and XRD were substantially those seen for the trimer. Fragments, with substantial intensities corresponding to the oligomers reported in Table I (m/e= 691, 693) were found.

TABLE I

Peak Positions (m/e) And Relative Intensities Observed In Mass Spectrometry Of Spinel Precursor[1]

| m/e | Intensity | Species |
|---|---|---|
| 329 | 19 | $MgAl(N(CH_2CH_2O)_3)N(CH_2CH_2O)_2HCH_2CH_2H^+$ |
| 347 | 80 | $Al_2(N(CH_2CH_2O)_3)N(CH_2CH_2O)_3H^+$ |
| 371 | 23 | $MgAl_2(N(CH_2CH_2O)_3)_2H^+$ |
| 387 | 51 | $MgAl_2(N(CH_2CH_2O)_3)_2OH^+$ |
| 431 | 20 | $MgAl_2(N(CH_2CH_2O)_3)_2HN(OCH_2CH_2)H_2^+$ |
| 474 | 13 | $MgAl_2(N(CH_2CH_2O)_3)_2HN(OCH_2CH_2)_2H^+$ |
| 518 | 100 | $HMgAl_2(N(CH_2CH_2O)_3)_3H^+$ |
| 562 | 39 | $HMgAl_2(N(CH_2CH_2O)_3)_3OCH_2CH_2^+$ |
| 691 | 17 | $MgAl_3(N(CH_2CH_2O)_3)_4H_2^+$ |
| 693 | 21 | $MgAl_3(N(CH_2CH_2O)_3)_4H_4^+$ |

[1]Analysis conducted using fast atom bombardment of vacuum dried sample (225° C.).

TABLE II

NMR Peak Positions and Tentative Assignments of Spinel Precursor[2]

| | Peak Positions | Tentative Assignments |
|---|---|---|
| $^1H$ NMR[a] | 2.55–2.85 (broad) | A, D, E |
| | 3.46 (sharp) | G |
| | 3.47–3.85 (broad) | BCF |
| $^{13}C$ NMR[a] | 50.56 (sharp) | A |
| | 53.09 | C and free TEA |
| | 54.66 | B |
| | 57.29 (major) | D and free TEA |
| | 59.83 | E |
| | 69.59 | F |
| $^{27}Al$ NMR[b] | 3.9 (minor) | Hexacoordinate Al |
| | 57.0 (major) | Tetracoordinate Al |

[2]Assignments based on comparison with pure Al-TEA complex.
[a]Sample dissolved in $CDCl_3$.
[b]Sample dissolved in $CD_2Cl_2$.

EXAMPLE 3

Preparation of CaAl$_2$(TEA)$_2$(OCH$_2$CH$_2$O)$_2$ by sequential addition of Al(OH)$_3$ and CaO Aluminum hydroxide hydrate [Al(OH)$_3$.xH$_2$O, 55 wt. percent Al$_2$O$_3$, Aldrich Chemical Company, Inc., Milwaukee, Wis.] TEA (Aldrich) and analytical, reagent grade EG (Mallincrodt, Paris, Ky.) were used as received. EG recovered from the reaction was distilled and recycled. Calcium oxide (99 wt. percent CaO, Strem Chemical, Inc., Newburyport, Mass.) was used as received.

Calcium oxide (3.73 g, 55 mmol CaO) was heated n 150 ml EG in a 250 ml flask under nitrogen so that water and some EG would distill off. After 24 h, the solution was filtered to remove undissolved CaO and CaCO$_3$. 135 g of solution was recovered with a ceramic yield of 1.94%, equivalent to 46.7 mmol of dissolved CaO indicating formation of ≈47 mmol of Ca(OCH$_2$CH$_2$O)$_2$.

In another flask, Al(OH)$_3$·xH$_2$O powder (45 g, 252 mmol Al$_2$O$_3$) was suspended with 1 equivalent ( 1 nitrogen per metal atom) of TEA (67 ml, 504 mmol) in EG (≈300 ml). The solution was mechanically stirred and heated to promote reaction, by distilling off EG coincident with the reaction by-product, H$_2$O. Additional EG was added as needed to lower the viscosity of the reaction. The solution cleared after 8 h reaction, indicating complete dissolution of the oxides to form the neutral complex TEA-Al. Solvent EG was distilled off to concentrate the solution to approximately 200 ml. The ceramic yield, 3.36% (as Al$_2$O$_3$) was determined using TGA. Equivalent molar amounts (135 g, 46.7 mmol CaO and 141.7 g, 46.7 mmol Al$_2$O$_3$, respectively) of each solution were added in a 250 ml flask with 7.33 g, 49.1 mmol, of TEA (Total concentration TEA is 1 nitrogen per metal center) and refluxed for 24 h. Product was recovered by treating as in above examples. Some material precipitated, that appeared to have the same composition as the material still in solution.

EXAMPLE 4

Dissolution of SiO$_2$ and Al(OH)$_3$.xH$_2$O using triethanolamine, N(CH$_2$CH$_2$OH)$_3$ Silica (1.5 g of 700 mesh, 25 mmol) was put into a 500 mL Schlenk flask with one metal equivalent aluminum hydroxide hydrate (50–57% as Al$_2$O$_3$, 2.6 g, 25 mmol). To the flask was added a slight excess of one equivalent of triethanolamine (24.25 mls 183 mmol) and 300 mL of ethylene glycol. The slurry was then distilled under N$_2$ to distill of ethylene glycol coincident with H$_2$O produced during the reaction. During the course of the reaction 250 mL of distillate was recovered. The reaction was run for 12 hours to give a slightly yellow solution.

EXAMPLE 5

Dissolution of a cordierite [2MgO·2Al$_2$O$_3$·5SiO$_2$] mixture of MgO/Al(OH)$_3$.xH$_2$O/SiO$_2$ using TEA Al(OH)$_3$.xH$_2$O (50–57.5% as Al$_2$O$_3$) (30.9 g, 322 mmol of Al) is placed in a 500 ml Schlenk flask along with 50 g of triethanolamine (335 mmol). 250 ml of ethylene glycol is added and the slurry was heated to distillation temperature under N$_2$. Ethylene glycol and water are distilled from the reaction mixture to drive the reaction to completion. To this solution are added 500 ml of additional ethylene glycol, 24.18 g SiO$_2$ (402 mmol) and 6.83 g MgO (322 mmol of 95% ceramic yield MgO). The solution is again heated to distillation and glycol and water are removed by distillation until the solution is clear. The solvent is removed under reduced pressure to give a hard, glassy polymer precursor. This brittle polymer is ground by mortar and pestle in the glovebox to give a clear tan solid. TGA analysis shows reproducibility in that the ceramic yield is always 39– 42%. On pyrolysis to 900° C., the product is phase pure μ-cordierite as established by XRD.

EXAMPLE 6

Lithium aluminosilicate

In the standard reaction, 1.0 equivalent of MOH (M=Li, Na, K, etc.) is reacted, with 1.0 equivalent of SiO$_2$, 1.0 equivalent of Al(OH)$_3$.xH$_2$O (53 wt. percent Al$_2$O$_3$) and 1.0 equivalent of triethanolamine (TEA) per metal, in excess EG with continuous distillative removal of water, followed by cooling. The resulting polymer is recovered by vacuum evaporation of solvent and/or washing with acetonitrile.

Figure 5:
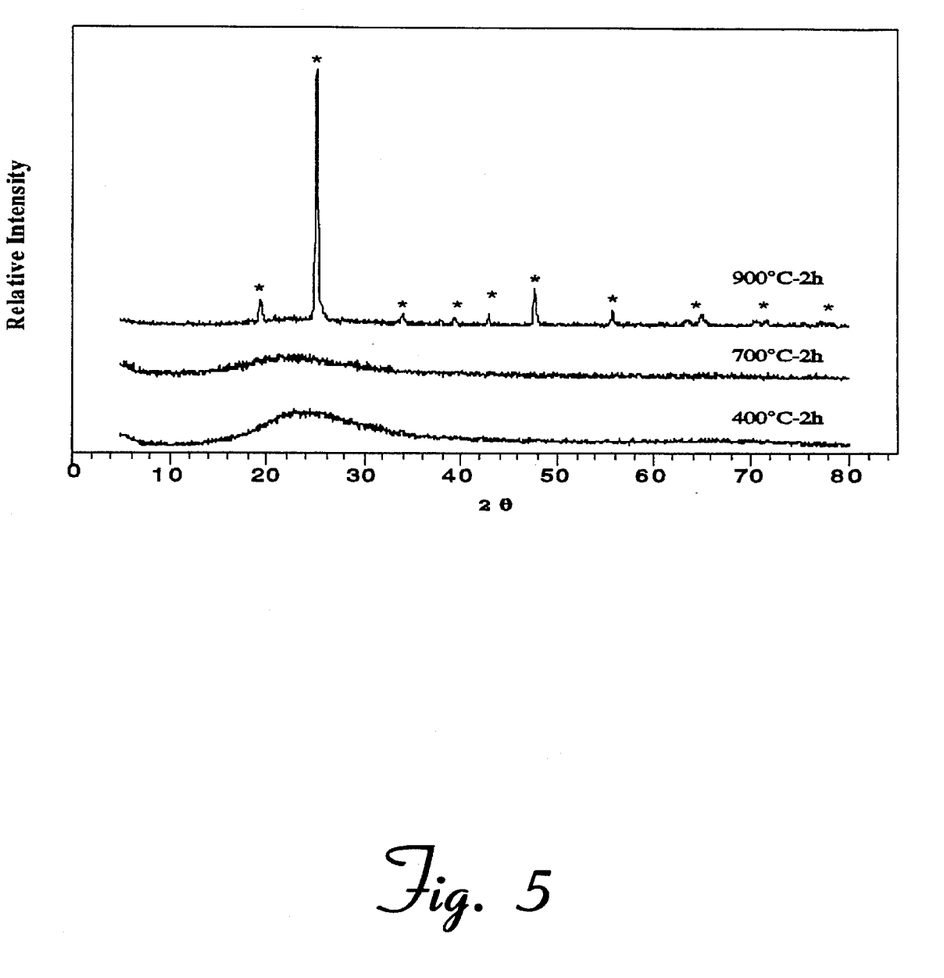
FIG. 5. XRD Powder Patterns for Lithium Aluminosilicate Samples Heated to Selected Temperatures. Samples ramped at 10° C. to temperature in flowing $O_2$ and held at temperature for 2h.

A mixture of 0.5 moles of LiOH (17 g, 57 wt. % LiOH by TGA), 0.5 moles of SiO$_2$ (30 g), 0.5 moles Al(OH)$_3$.xH$_2$O (38 g, 53 wt %. Al$_2$O$_3$ by TGA), 3.0 moles of TEA (180 g), and 500 mL of EG are placed in a 1 L flask equipped with a still head. The mixture is heated to ≈200° C. under N$_2$ with constant mechanical stirring. The silica, alumina and alkali hydroxide readily dissolve with continuous distillation of EG and coincident removal of H$_2$O formed as by-product. The reaction goes clear and is complete in 4–5 h, when 350–400 mL of EG have distilled off. The clear solution becomes increasingly viscous as EG is removed. The resulting product is dried under dynamic vacuum at temperatures of 200°–250° C. The microstructural evolution of the precursor on heating in air is seen in FIG. 5.

COMPARATIVE EXAMPLE 1

Dissolution of a Monopotassium Aluminosilicate (KAlSiO$_4$) Precursor

Potassium Hydroxide (5.12 g, 82 mmol of 95% KOH) was added to a flask with 50 mL of ethylene glycol. The slurry was heated under N$_2$ until all of the KOH dissolved. 7.6 g of Al(OH)$_3$.xH$_2$O (54.8% as Al$_2$O$_3$, 82.3 mmol) was introduced to a clean flask. The dissolved KOH solution was then added to this flask. An additional 100 mL of glycol was used to ensure that all of the KOH was washed into the flask. The resulting solution was brought to reflux under N$_2$ for 1 hour and the solution was allowed to distill until all of the Al(OH)$_3$ had dissolved (≈1 h) as evidenced by a clear solution.

The solution was allowed to cool and 5.0 g of fumed SiO$_2$ (82 mmol) was added. The solution was again refluxed. Ethylene glycol was distilled off slowly over a period of 10 h. The object of the distillation was to remove product water formed from the anticipated reaction of the potassium glyocolato aluminum with SiO$_2$. At the end of 10 h, the solution remained opaque as the SiO$_2$ powder did not react under conditions where it would usually react in the space of 20 min, if excess akali base was added.

EXAMPLE 7

Dissolution of a Monopotassium Aluminosilicate (KAlSiO$_4$) Precursor

The unreacted final solution from Example 13 was then mixed with 0.97 equivalents (12 g, 80 mmol) of TEA and heated to distill for 1 h. The opaque solution turned clear during the 1 h reflux. The resulting preceramic polymer can be used to make Ka/SiO$_4$ based zeolites or amorphous ceramic products or crystalline non-zeolite products.

EXAMPLE 8

MgAl$_2$(TEA)$_2$(OCH$_3$)$_2$ by sequential addition of Al(OH)$_3$ and Mg(OMe)$_2$ Magnesium metal turnings, 5.00 g, 206 mmol (Aldrich Chemical) were placed in a 250 mL round bottomed flask fitted with a reflux condenser and a nitrogen inlet. To the flask were added a magnetic stir bar and 100 mL of methanol, MeOH, freshly distilled from magnesium methoxide and a pinhead quantity of HgCl$_2$ (Alfa Inorganics). An exothermic reaction ensued immediately, with evolution of H$_2$. After the gas evolution had slowed, the reaction was heated to reflux with an oil bath to complete the dissolution process. The resulting cloudy solution of magnesium methoxide, Mg(OMe)$_2$, was diluted with 50 mL of methanol, filtered through a 0.2 μm syringe filter. The ceramic yield of this solution was found to be 4.96 wt % MgO, or 1.23 mmol Mg/g of solution.

A 9.60 g (11.8 mmol Mg) aliquot of the solution was mixed with 4.46 g of [TEA-Al]$_4$, prepared as in Example 2, of 25.8 wt % ceramic yield (11.8 mmol Al$_2$O$_3$) and 10 mL of MeOH in a 50 mL pear-shaped flask fitted with a magnetic stir bar, nitrogen inlet and a reflux condenser. The flask was heated to reflux overnight, resulting in a clear, slightly yellowish solution. The methanol was removed from the solution under reduced pressure, giving a quantitative yield of a yellowish, friable solid.

EXAMPLE 9

Dissolution of SiO$_2$ and Al(OH)$_3$.xH$_2$O using triethanolamine N(CH$_2$CH$_2$OH)$_3$

A mullite precursor was synthesized directly from SiO$_2$, Al(OH)$_3$.xH$_2$O, ethylene glycol (EG) and triethanolamine (TEA), by a direct low temperature route. Al(OH)$_3$.xH$_2$O (53.5% Al$_2$O$_3$) (3 mmol, 31.43 g), TEA (3 mmol, 45 mL) and excess EG (300–350 mL) were placed in a 500 mL schlenk flask. The mixture was heated to the EG distillation temperature, under N$_2$, with constant mechanical stirring. The Al(OH)$_3$.xH$_2$O dissolves readily with continuous, slow distillative removal of EG and byproduct water. The reaction goes clear in 1–2 h after 250–300 mL of EG distills off and a clear yellow solution is obtained containing the neutral complex TEA-Al. The reaction is allowed to cool to room temperature.

SiO$_2$ (2 mmol, 6.77 gm.), TEA (2 mmol, 15 mL) and excess EG (200 mL) are added to this solution. The mixture is again heated under N$_2$, with constant mechanical stirring. As the distillation continues, silica dissolves and in 1–2 h, the reaction goes clear. The reaction is stopped after 200–250 mL of EG and byproduct water have distilled off. A clear golden yellow viscous solution is obtained. This solution is vacuum dried at ≈210° C. for 2–3 h to remove excess EG and TEA, if any. On cooling, a hard brittle polymer is obtained which is freeze-fractured (alternate cooling in liquid N$_2$ and warming in hot water bath), transferred to a container. The yield is quantitative. The material gives phase pure mullite (by XRD, x-ray photoelectron spectroscopy and DRIFTS) on heating ground polymer samples in air to 1350° C. for 1 h.

While the forms of the invention herein disclosed constitute presently preferred embodiments, many others are possible. It is not intended herein to mention all of the Dossible equivalent forms of ramifications of the invention. It is understood that the terms used herein are merely descriptive rather than limiting and that various changes may be made without departing from the spirit or scope of the invention.

What is claimed is:

1. A neutral or mixed ionic/neutral polymetallooxane comprising the moiety:

wherein M$^1$ is selected from the group consisting of trivalent or tetravalent Al, or Ga, or tetravalent, pentavalent, or hexavalent Si, Ge, Sn, Ti, Zr, and Hf; n is 2, 3 or 4 when M$^1$ is Al, or Ga; and n is 3, 4, 5, or 6 when M$^1$ is Si, Ge, Sn, Ti, Zr, or Hf;

R$^1$ and R$^2$ are independently selected from the group consisting of H, OH, C$_{1-8}$ alkyl, C$_{1-6}$ alkoxy, C$_{2-8}$ alkenyl, C$_{6-12}$ aryl, C$_{1-8}$ hydroxyalkyl, C$_{1-8}$ thioalkyl, C$_{2-12}$ alkoxyalkyl, C$_{4-20}$ heteroaromatic, C$_{1-10}$ alkylsilane, C$_{1-10}$ alkylsiloxane and combinations thereof;

O' is bonded to M$^1$, M$^2$ or H wherein

M$^2$ is selected from the group consisting of Si, Ge, Sn, Al, Ga, Ti, Zr, Hf, an ammonium species, a phosphonium species, a Group Ia metal of the Periodic Table, and a IIa metal of the Periodic Table;

wherein when one O' is bonded to M$^1$, n is 2 or 3 when M$^1$ is Al, or Ga, and at least one O' is bonded to M$^2$; wherein when one O' is bonded to M$^1$, n is 3, 4, or 5 when M$^1$ is Si, Ge, Sn, Ti, Zr, or Hf and at least one O' is bonded to M$^2$; and wherein when two O' are bonded to M$^1$ and M$^1$ is Si, Ge, Sn, Ti, Zr, or Hf, n is 3 or 4 and at least one O' is bonded to M$^2$; and R$^3$ is independently selected from the group consisting of (CR$_2$)$_y$, (CR$_2$CR$_2$)$_y$NR(CR$_2$)$_y$, [(CR$_2$CR$_2$)$_y$O]$_y$-(CR$_2$)$_y$, and combinations thereof wherein R is selected from the group consisting of H, OH, C$_{1-8}$ alkyl, C$_{1-6}$ alkoxy, C$_{2-8}$ alkenyl, C$_{6-12}$ aryl, C$_{1-8}$ hydroxyalkyl, C$_{1-8}$ thioalkyl, C$_{2-12}$ alkoxyalkyl, C$_{4-20}$ heteroaromatic, C$_{1-10}$ alkylsilane, C$_{1-10}$ alkylsiloxane and combinations thereof, and where y is a number from 1 to 10 and wherein said polymetallooxane contains at least one M$^2$.

2. The polymetallooxane of claim 1 wherein n is 2, 3, or 4;

M$^1$ is Al; and O' is bonded to M$^1$ (4-n) times.

3. The polymetallooxane of claim 1 wherein n is 3, 4, or 5;

M$^1$ is Si; and O' is bonded to M$^1$ (5-n) times.

4. The polymetallooxane of claim 2 wherein R$^3$ contains at least one nitrogen atom.

5. The polymetallooxane of claim 3 wherein R$^3$ contains at least one nitrogen atom.

6. The polymetallooxane of claim 4 wherein M$^2$ is a group Ia metal.

7. The polymetallooxane of claim 4 wherein M$^2$ is a group IIa metal.

8. The polymetallooxane of claim 5 wherein M$^2$ is a group Ia metal.

9. The polymetallooxane of claim 6 wherein M$^2$ is a group IIa metal.

10. The polymetallooxane of claim 1 wherein all $M^1$ atoms are Al.

11. The polymetallooxane of claim 1 wherein some $M^1$ atoms are Al.

12. The polymetallooxane material containing the heterocyclic moiety:

wherein M is Al, Ga, Si, Ge, Sn, Ti, Zr, or Hf; wherein when M is Al, or Ga, p is 0 or 1; and when M is Si, Ge, Sn, Ti, Zr, or Hf, p is 1, 2, or 3; when M is Al, or Ga, and p is 1, $Q^+$ is a group Ia counterion, group IIa counterion, or ammonium counterion of the formula $R_4N^+$ or phosphonium counterion of the formula $R_4P^+$, and when p=0, $Q^+$ is not present; and when M is Si, Ge, Sn, Ti, Zr, or Hf and p is 2 or 3, $Q^+$ is a group Ia counterion, group IIa counterion, or ammonium counterion of the formula $R_4N^+$, or phosphonium counterion of the formula $R_4P^+$, and when p=1, $Q^+$ is not present; wherein R is independently selected from the group consisting of H, OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane and combinations thereof; wherein Z is the residue of an amine reactant; and wherein n is from 1 to about 150.

13. The polymetallooxane of claim 12 wherein all $M^1$ atoms are Al.

14. The polymetallooxane of claim 13 wherein n is 1.

15. The polymetallooxane of claim 13 wherein n is 2–20.

16. The polymetallooxane of claim 13 wherein n is 21–150.

17. The polymetallooxane of claim 12 wherein some $M^1$ atoms are Al.

18. A neutral or neutral/anionic polymetallooxane comprising the moiety:

wherein when $M^1$ is Al, or Ga, n is 2, 3 or 4; and when $M^1$ is Si, Ge, Sn, Ti, Zr, or Hf, n is 3, 4 or 5;

wherein O' is bonded to $M^1$, $M^2$, or H, wherein $M^2$ is Al, Ga, Si, Ge, Sn, Ti, Zr, or Hf, and the number of O' bonded to $M^1$ is such that $M^1$ is trivalent or tetravalent when $M^1$ is Al, or Ga, and tetravalent, pentavalent, or hexavalent when $M^1$ is Si, Ge, Sn, Ti, Zr, or Hf, wherein when $M^1$ is tetravalent Si and n is 3, the polymetallooxane contains three or more Si linked by —O'—$R^3$—C($R^1$)($R^2$)—O— linkages;

wherein $R^1$ and $R^2$ are independently selected from the group consisting of H, OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, and $C_{1-10}$ alkylsiloxane;

wherein each $R^3$ individually is an organic linking group optionally substituted by OH, $C_{1-8}$ alkyl, $C_{1-6}$ alkoxy, $C_{2-8}$ alkenyl, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, or $C_{1-10}$ alkylsiloxane, and said optionally substituted organic linking group is selected from the group consisting of $C_{1-10}$ alkylene, $C_{4-8}$ cycloalkylene, $C_{1-10}$ alkylene containing interspersed heteroatoms of nitrogen, sulfur, or phosphorus, and $C_{4-8}$ cycloalkylene containing interspersed heteroatoms of nitrogen, sulfur, or phosphorus;

wherein when at least one $M^1$ is anionic, said polymetallooxane further contains sufficient cationic counterions such that said polymetallooxane is electrically neutral, said polymetallooxane prepared by the process comprising:

a) selecting a metaloxy compound capable of supplying an $M^1$ metal;

b) reacting said metaloxy compound with a polyhydroxy compound in the presence of an organic amine, wherein when said organic amine is a polyolamine and all $M^1$ are silicon, the molar ratio of polyolamine to silicon is less than about 1.5:1;

c) removing substantially all the water produced by said reacting b);

d) recovering a neutral or mixed netural/anionic polymetallooxane product.

19. The polymetallooxane of claim 18, wherein when all $M^1$ are Si, said polymetallooxane contains at least two Si.

20. The polymetalloxane of claim 19 wherein $M^1$ and $M^2$ are selected from the group consisting of aluminum, silicon, and mixtures thereof.

21. The polymetallooxane of claim 19 wherein said counterion is a cation of a group Ia or IIa metal, or an ammonium or phosphonium ion.

22. A neutral or mixed neutral/anionic polymetallooxane prepared by the process of:

a) reacting a metaloxy component comprising one or more hydroxides, oxides, or a hydrate thereof of at least one metal selected from the group consisting of Al, Ga, Si, Ge, Sn, Ti, Zr, and Hf; with b) a polyhydroxyl compound containing two or more hydroxyl groups; and c) an amine or alkanolamine to form a reaction mixture;

d) removing water from said reaction mixture; and recovering a neutral or mixed neutral/anionic polymetallooxane product.

23. The neutral or mixed neutral/anionic polymetallooxane of claim 22 wherein said metaloxy component comprises one or more metaloxy compounds selected from the group consisting of the oxides and hydroxides of aluminum and silicon, and hydrates thereof.

24. The neutral or mixed neutral/anionic polymetallooxane of claim 23 wherein said metaloxy component further comprises a hydroxide or oxide of magnesium or calcium, or hydrate thereof.

25. The neutral or mixed neutral/anionic polymetallooxane of claim 22 wherein said polyhydroxyl compound comprises ethylene glycol and said alkanolamine comprises triethanolamine.

26. The neutral or mixed neutral/anionic polymetallooxane of claim 22 wherein said process further comprises:

e) removing at least a portion of said polyhydroxyl compound from said reaction mixture prior to recovering said polymetallooxane.

* * * * *

UNITED STATES PATENT AND TRADEMARK OFFICE
CERTIFICATE OF CORRECTION

PATENT NO. : 5,614,596
DATED : March 25, 1997
INVENTOR(S) : Richard M. Laine, Clint R. Bickmore, Kurt F. Waldner It is certified that error appears in the above-indentified patent and that said Letters Patent is hereby corrected as shown below:

Column 24, line 66, "claim 6" should read --claim 5--.

Signed and Sealed this

Twenty-eighth Day of July, 1998

Attest:

BRUCE LEHMAN

Attesting Officer     Commissioner of Patents and Trademarks